United States Patent [19]

Jundanian

[11] 4,347,851
[45] Sep. 7, 1982

[54] VITAL SIGNS MONITOR

[75] Inventor: Richard H. Jundanian, Whitinsville, Mass.

[73] Assignees: Norman S. Blodgett; Gerry A. Blodgett, both of Worcester, Mass.; part interest to each

[21] Appl. No.: 199,286

[22] Filed: Oct. 21, 1980

[51] Int. Cl.³ .............................................. A61B 5/02
[52] U.S. Cl. .................................. 128/668; 128/672; 128/673; 364/417
[58] Field of Search ............... 128/668, 670, 673, 672, 128/695, 700; 364/415, 417

[56] References Cited
PUBLICATIONS

Loonen, J., "Blood Pressure by Oscillometry," Med. Elec., Apr. 1978, pp. 57–63.

Primary Examiner—Kyle L. Howell
Assistant Examiner—J. C. Hanley
Attorney, Agent, or Firm—Blodgett & Blodgett

[57] ABSTRACT

A vital signs monitor which includes a sensor which is applied to the main artery of a patient for detecting the heart beat and blood pressure and producing electrical pulses in waveform. A computer is connected to the sensor for receiving the waveform pulses, converting the waveform pulses into digital signals and calculating the heart rate, blood pressures and rate-pressure product. A visual display screen is connected to and controlled by the computer for displaying the heart rate, blood pressure and rate-pressure product in digital form.

5 Claims, 11 Drawing Figures

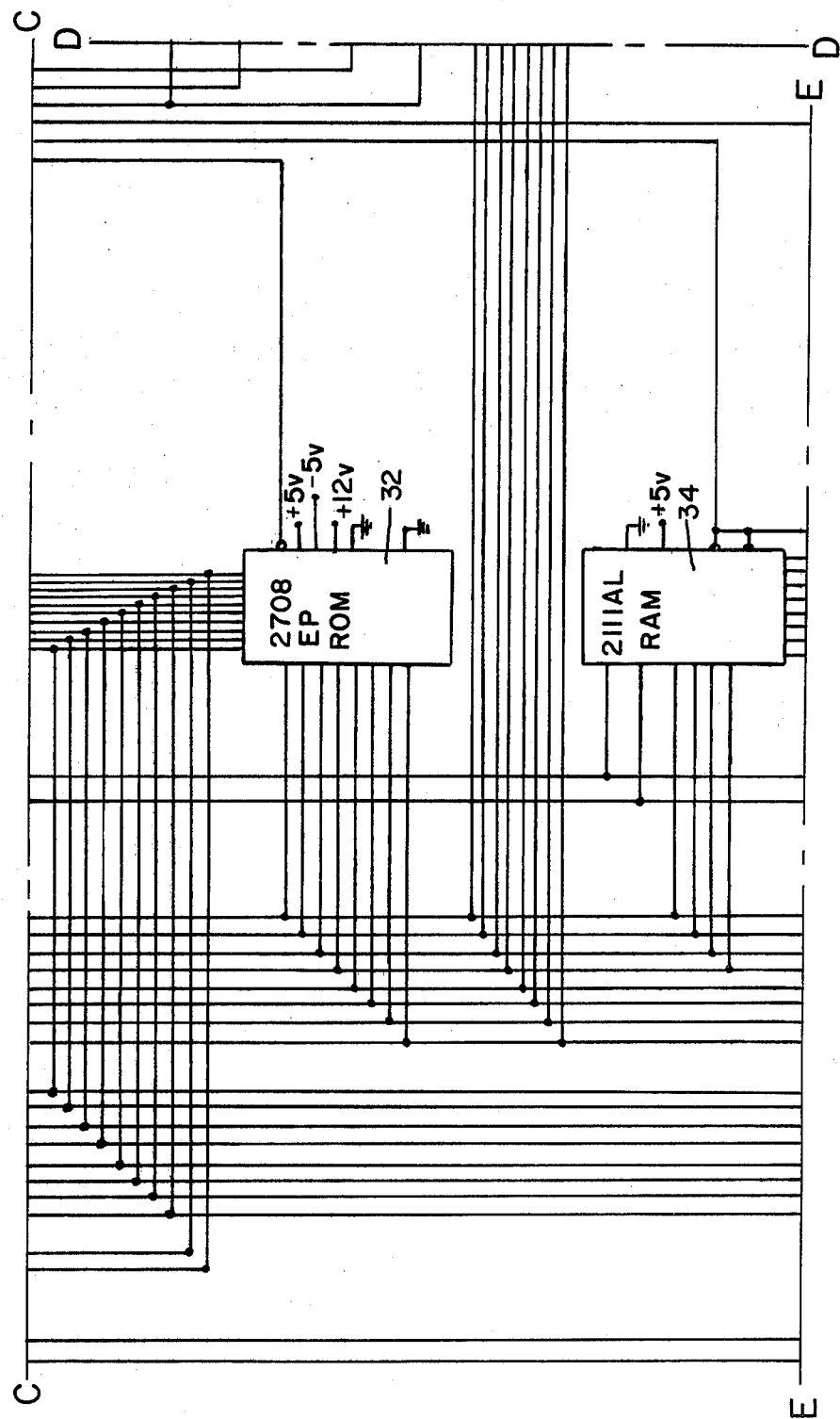

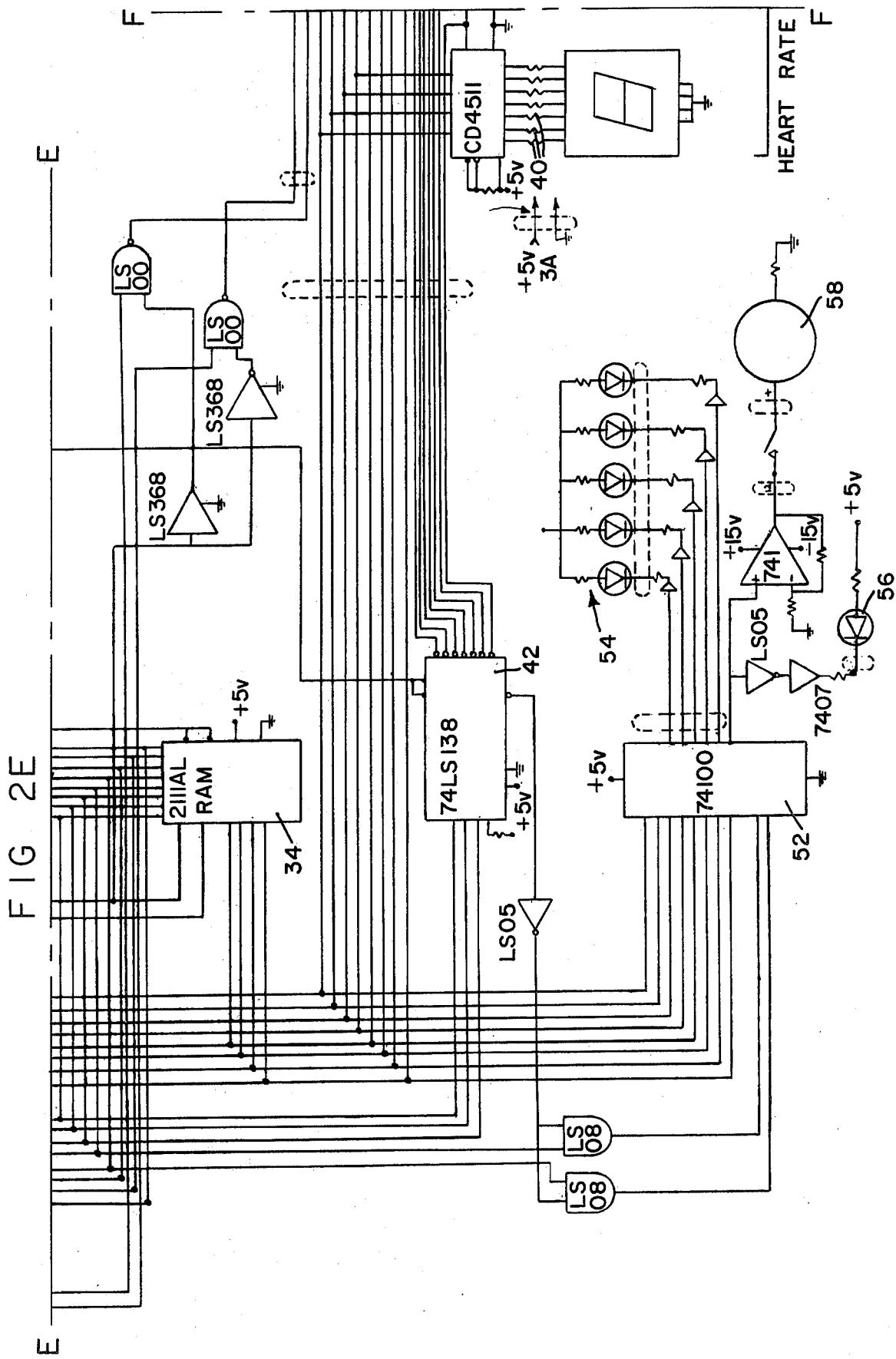

VITAL SIGNS MONITOR

BACKGROUND OF THE INVENTION

The present invention is directed generally to the monitoring of a patient's vital signs, particularly during open-heart surgery.

Open-heart surgery requires precise intensive monitoring of the patient's condition throughout the operation and during the recovery period. Pulmonary and radial arterial pressures are among the many parameters constantly monitored during open-heart surgery. These pressures, along with many other parameters, are important to the anesthesiologist. One of these other parameters is the rate-pressure product. The rate-pressure product is indirectly related to the myocardial oxygen supply and can be obtained from the product of the systolic pressure and the heart rate.

Present monitoring systems include a transducer and amplifier connected to a catheter implanted in the patient's radial artery. The transducer amplifier and EKG amplifier is connected to a CRT (cathode ray tube) screen which displays the wave forms of the heart rate and systolic pressure. The anesthesiologist reads the wave forms and calculates the rate-pressure product. In addition to being time consuming, this procedure is prone to error, because of the poor resolution of the CRT screen and because of the possibility of matching the heart rate with the wrong blood pressure wave form when calculating the rate-pressure product. These and other difficulties have been obviated by the present invention.

It is, therefore, an outstanding object of the invention to provide a vital signs monitor which provides automatic digital display of vital sign parameters.

Another object of the invention is the provision of a vital signs monitor which automatically calculates and displays the rate-pressure product from the systolic pressure and heart rate.

A further object of the present invention is the provision of a vital signs monitor that is capable of averaging the rate-pressure product for a plurality of heart beats and is capable of being selectively programmed to display the average rate-pressure product for a selected number of heart beats.

It is another object of the instant invention to provide a vital signs monitor that has an alarm and is selectively programmable for a high rate-pressure value and a low rate-pressure value, in such a way that the alarm is activated when either the low or the high value is displayed.

With these and other objects in view, as will be apparent to those skilled in the art, the invention resides in the combination of parts set forth in the specification and covered by the claims appended hereto.

SUMMARY OF THE INVENTION

In general, the invention consists of a vital signs monitor having a sensor for monitoring the heart beat and blood pressure of a patient, having a computer and having a digital display screen connected to the computer. The sensor produces electrical pulses in a waveform that is indicative of the heart rate and blood pressure. The computer receives the waveform pulses from the sensor, converts the waveform pulses into digital signals, and calculates the rate-pressure product which is visually displayed in digital form on the display screen together with the heart rate and blood pressure.

More specifically, the computer is programmable for selectively establishing a low rate-pressure product value and high rate-pressure product value; it includes an alarm which is activated when either the low value or the high value is reached. The computer is also capable of averaging the rate-pressure product value for a plurality of heart beats and is selectively programmable to cause the average rate-pressure product value for a selected number of heart beats to be displayed on the screen.

BRIEF DESCRIPTION OF THE DRAWINGS

The character of the invention, however, may be best understood by reference to one of its structural forms, as illustrated by the accompanying drawings, in which:

FIGS. 2A–2G are portions of a schematic diagram of the computer and digital display, the complete diagram being formed by arranging the portions 2A–2G along lines 2B–2G.

DESCRIPTION OF THE PREFERRED EMBODIMENT

Figure 1:
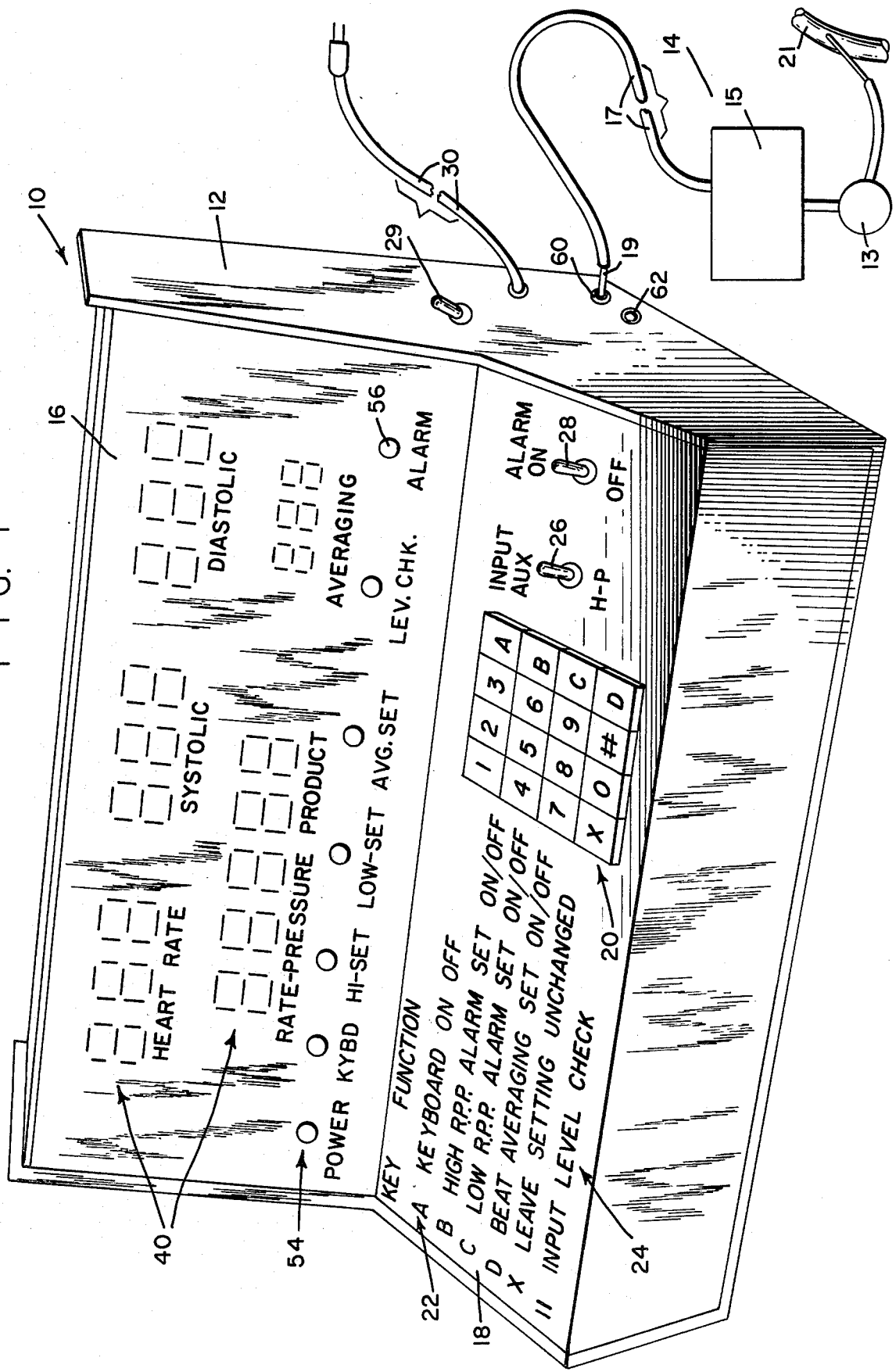
FIG. 1 is a perspective view of a vital signs monitor embodying the principles of the present invention.
Figure 2A:
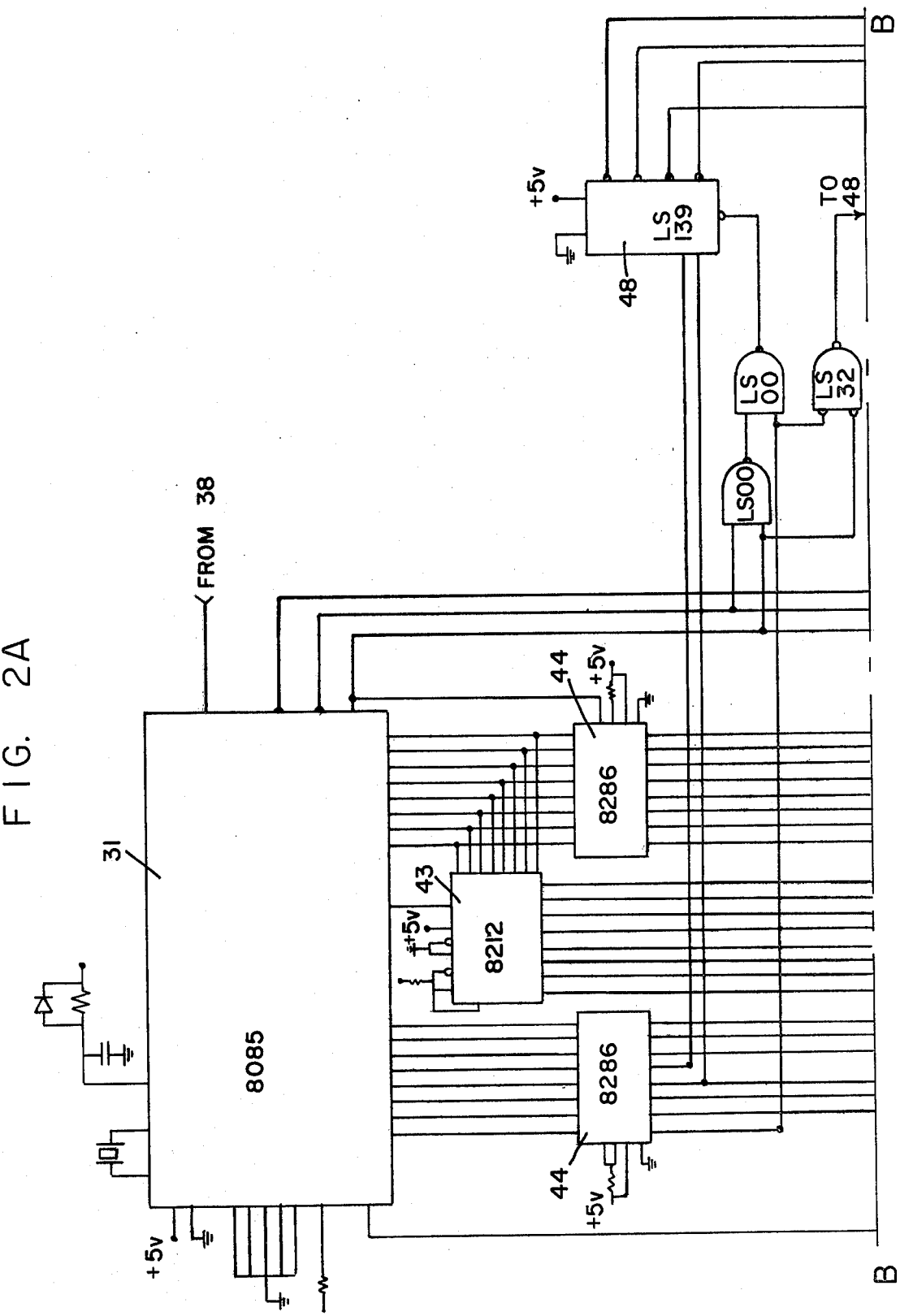
Figure 2B:
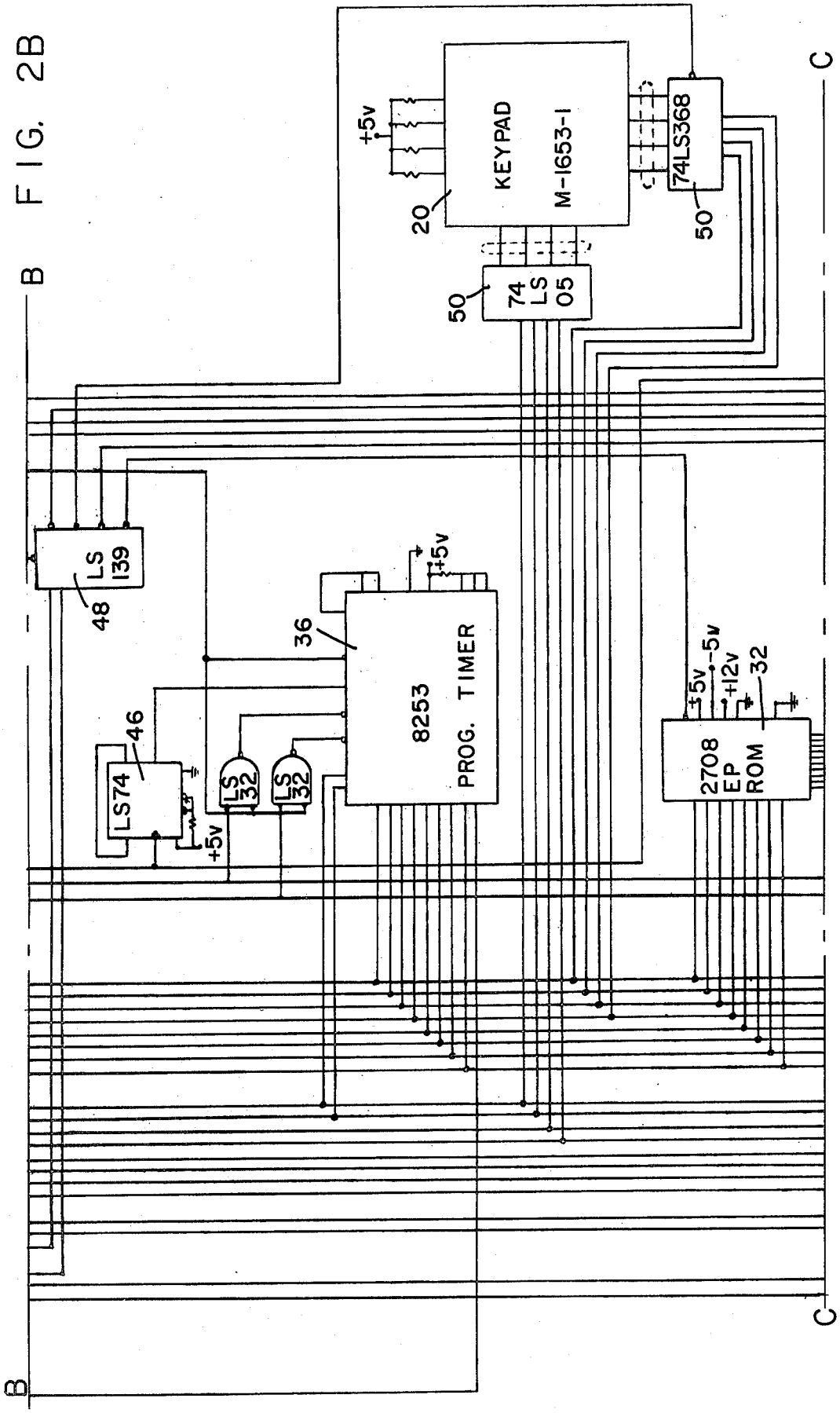
Figure 2D:
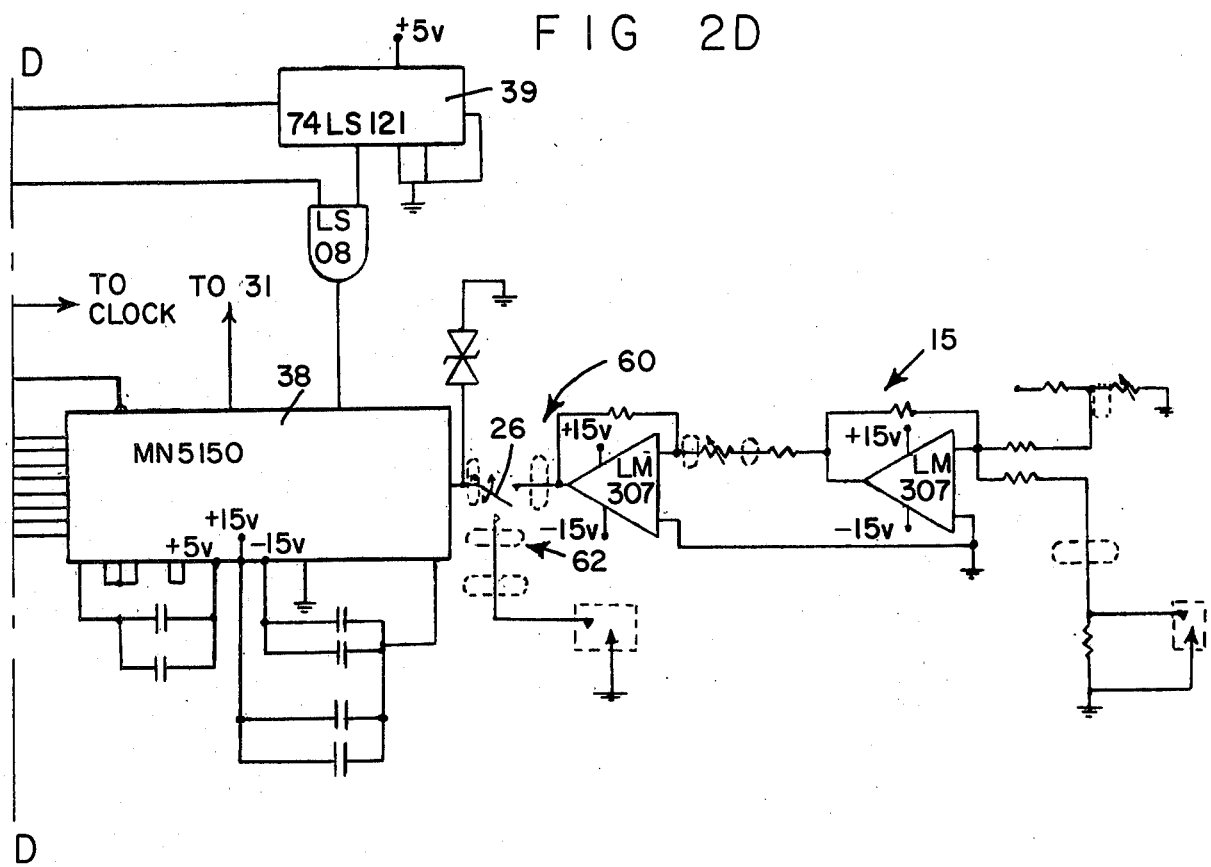
Figure 2F:
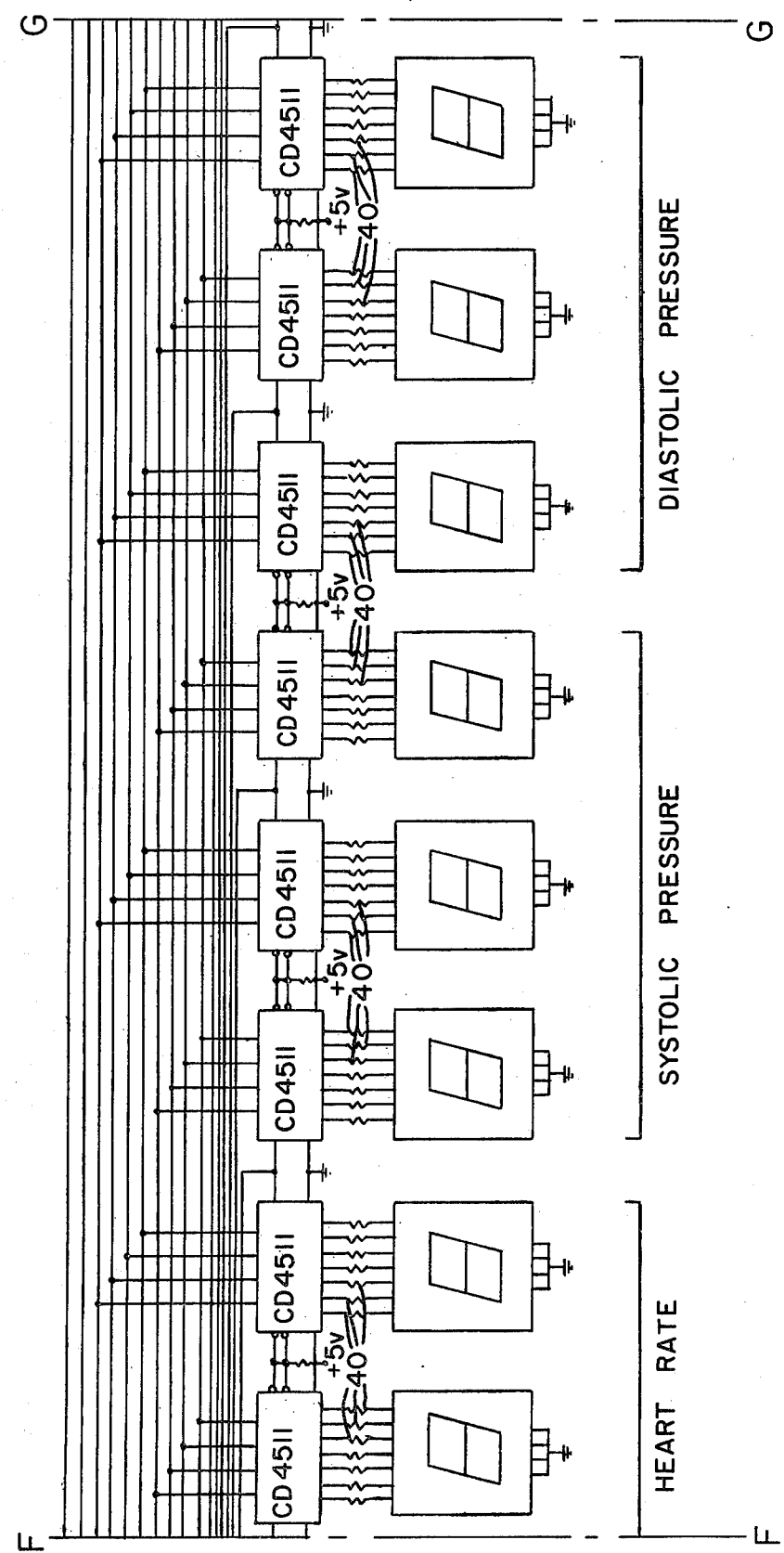
Figure 2G:
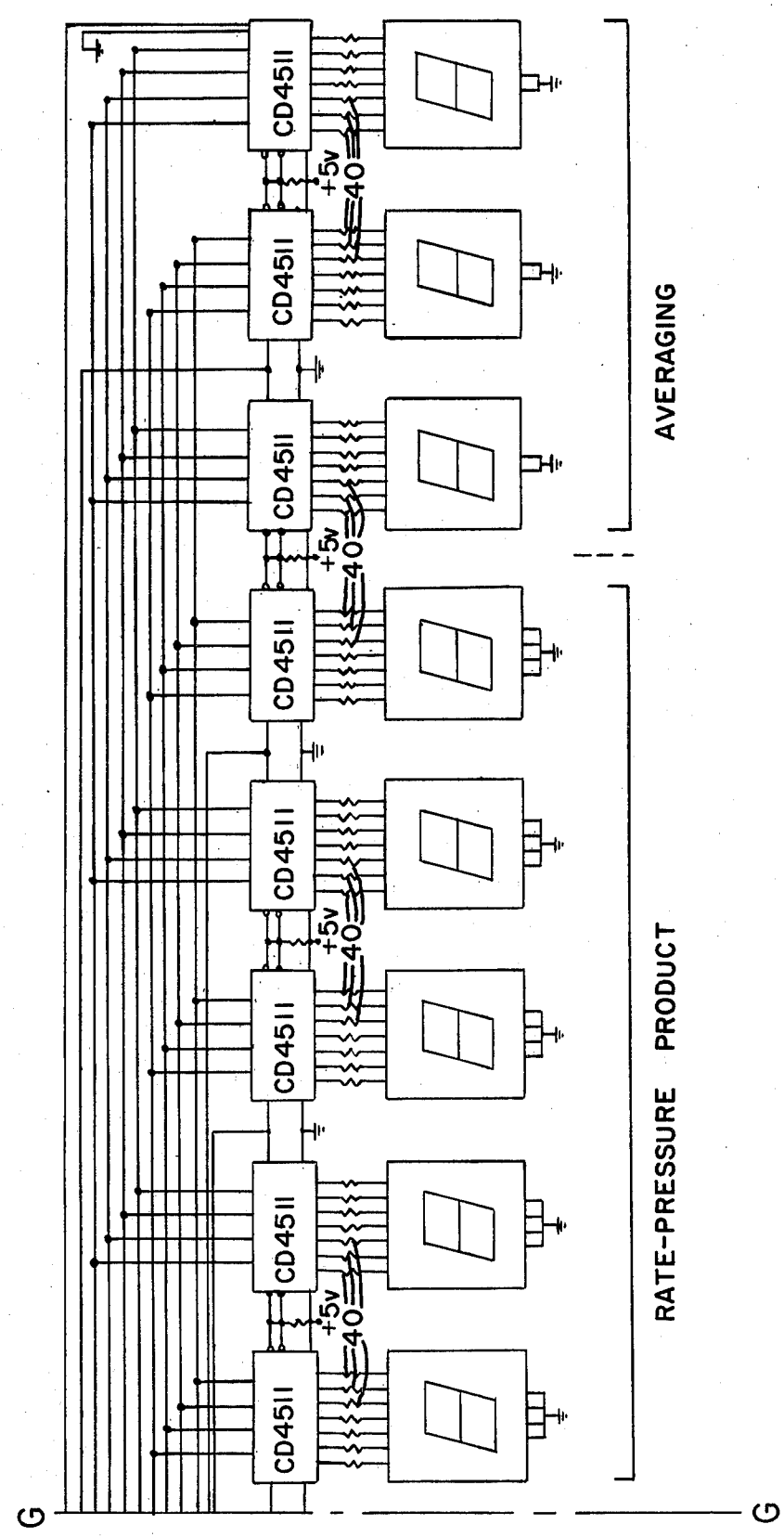
Figure 3:
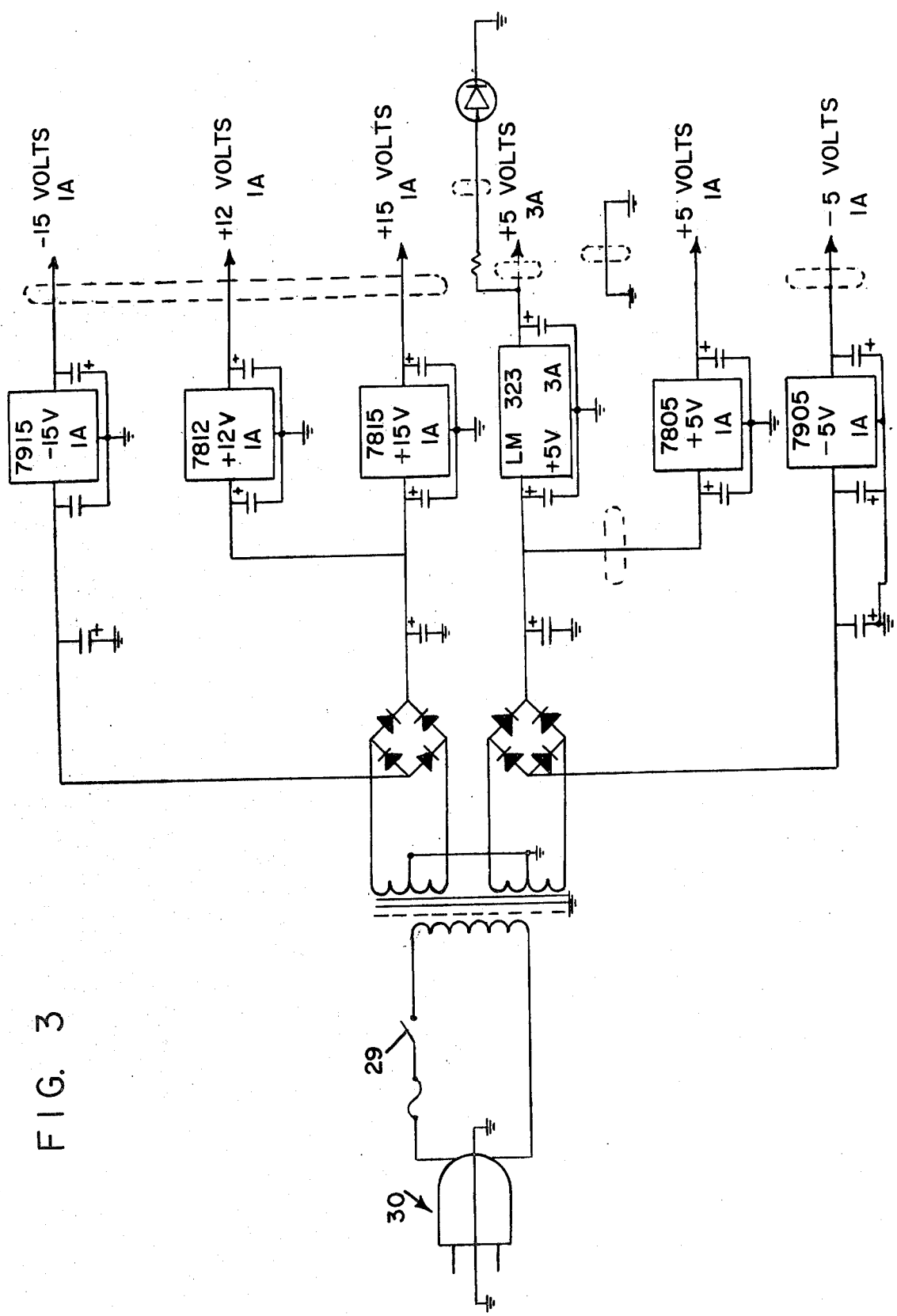
FIG. 3 is a schematic diagram of the power circuit for the monitor circuit shown in FIGS. 2A–2G.

Referring first to FIG. 1, which best shows the general features of the invention, the vital signs monitor, indicated generally by the reference numeral 10, is shown enclosed in a console 12. The vital signs monitor 10 is provided with a sensor, generally indicated by the reference numeral 14, which consists of a transducer catheter unit 13 connected to a carrier amplifier 15. The catheter transducer unit is a Bentley Trantec Model 400 and the amplifier is a Hewlett-Packard 8805B. The catheter of unit 13 is connected to a radial artery 21 of a patient. The sensor 14 produces electrical pulses in a waveform that is indicative of the heart beat and blood pressure of the patient. The waveform pulses are transmitted to the computer within the console by means of the wire connection 17 and phono plug 19.

The monitor 10 also includes a display screen 16 consisting of LED (light emitting diode) matrices for displaying the heart rate, systolic blood pressure, and diastolic blood pressure in digital form. There is also a matrix for generating the rate-pressure product and a matrix for averaging, both of which are to be described. The front of the console 12 contains a control panel 18 which includes a keyboard 20 that contains labeled key switches. The key indicia, generally indicated by the reference numeral 22, and short-form function indicia, generally indicated by the reference numeral 24, are printed on the control panel to assist the operator in using the keyboard 20. These function indicia correspond to the labels on the display board 16 beneath each group of LED matrixes. Standard units are assumed, including heart rate in beats/min., pressures in mmHg, and rate-pressure product in beats-mmHg/min. The control panel 18 also includes a MODE switch 26, to be described as well as an audio alarm switch 28. The console also includes an ON-OFF switch 29 and is connected to a conventional source of electrical power by means of an electrical cord 30.

Console 12 contains a computer for receiving the waveform pulses from the sensor 14. The computer digitizes and processes the waveform for display on the screen 16 in the form of heart rate, systolic and diastolic pressures, and the rate-pressure product.

Referring to FIGS. 2A-2G and 3, the computer includes an INTEL 8085 CPU (central processing unit) 31 and memory units 32 and 34. Chips 32 are 1K×8 ROM (read only memory), Motorola type 2708, and chips 34 are 256×8 RAM, (random access memory) INTEL type 8111. Chip 36 has three presettable down counters tha are used to accurately time the sampling and the period of the waveform. An 8-bit A/D (analog-to-digital) converter 38 digitizes the waveform in 2.5 microseconds at 10.0 millisecond intervals. Converter 38 is connected to a one-shot multivibrator 39. The keys in keyboard 20 are used to program high and low rate-pressure product alarm values in addition to setting the averaging of beats from one to 255. All these electronic elements, including a 74LS138 decoder 42 which controls the LED's 40 used to display the results are decoded with a 74LS139 decoder 48 and driven via a 8212 latch 43 and 8286 bus drivers 44. The computer has an 8-bit data bus and a 16-bit multiplexed address bus.

Other elements in the computer circuit shown in FIGS. 2A-2G include a flip-flop 46 for dividing signals to the timer 36. Inverters 50 connect the keyboard 20 to the busses. A latch 52 is connected to a plurality of function lights consisting of LEDs generally indicated by the reference numeral 54. The function lights 54 are shown and labeled on the display board 16 in FIG. 1. Latch 52 is also associated wih the alarm system for indicating a predetermined high and low rate-pressure value. The alarm system includes an LED light 56 and an audio signal device or buzzer 58.

The input waveform signal from the sensor 14 is received by the converter 38 through a primary input connection shown as a phono jack 60 in FIG. 1. An auxiliary input connection or phono jack 62 is used with a blood pressure signal which varies between zero and five volts DC. A zero value of volts, when fed into the auxiliary input corresponds to zero mmHg after the computer samples it. Likewise, 5.0 volts corresponds to 255 mmHg. This input is incorporated into the device, so that the operator can monitor any blood pressure signal with just the use of an external wave conditioning unit to condition the waveform before feeding it into the computer. This wave conditioning unit would contain appropriate level shifting and gain controls to match the waveform to the auxiliary input specifications. This gives the monitor the added flexibility necessary for use not only in the operating room, but also as a bedside monitor in an intensive care unit.

The primary input connection 60 is specifically designed to be used with a Hewlett-Packard 8805B carrier amplifier 64. There is no need for an external wave conditioning unit to be used with the primary input, because the computer already has one built in that conditions the signal coming from the amplifier 64. The computer may be connected in the primary mode or the auxiliary mode by means of the previously mentioned input switch 26.

Figure 4:
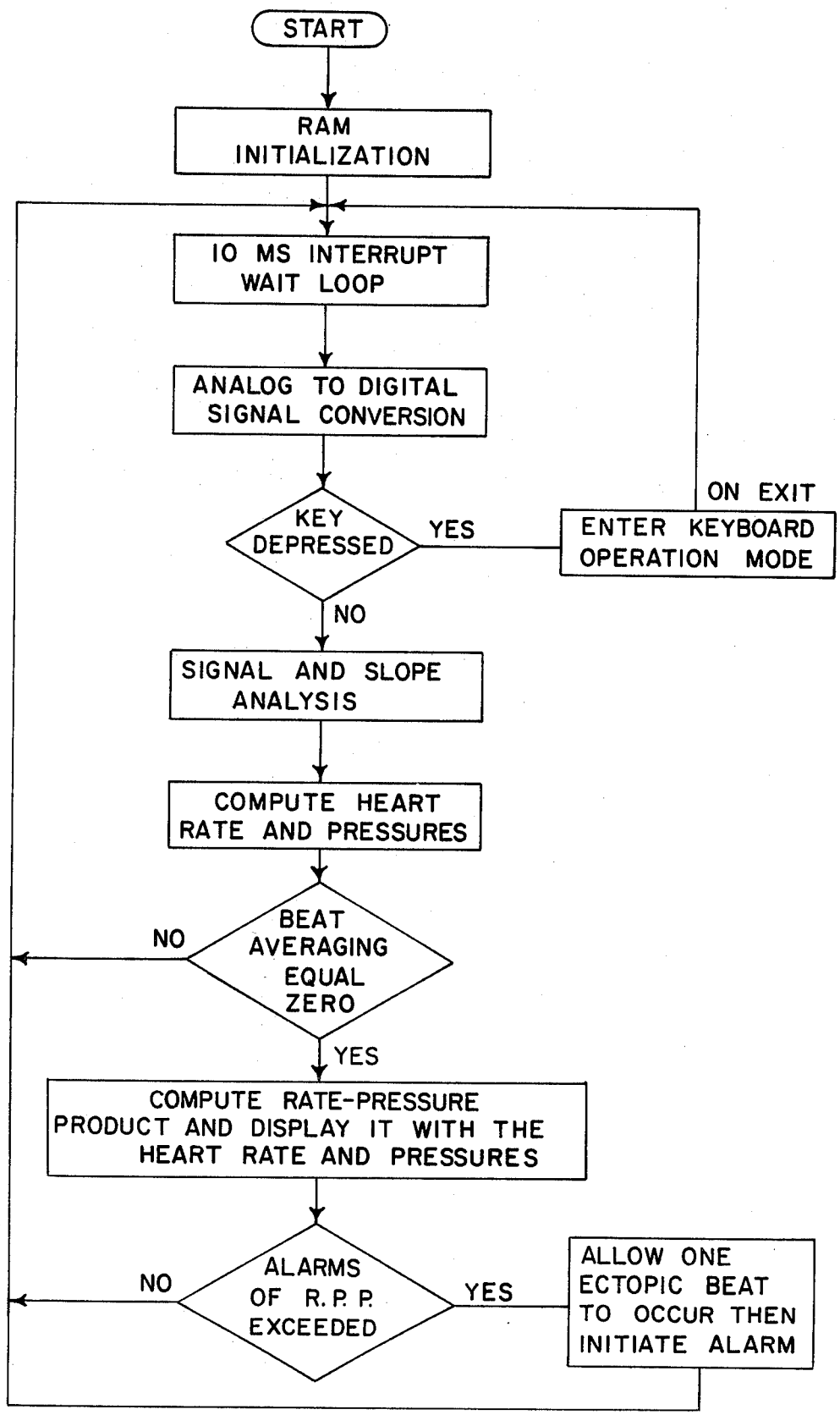
FIG. 4 is a software block diagram for the monitor.
Figure 5:
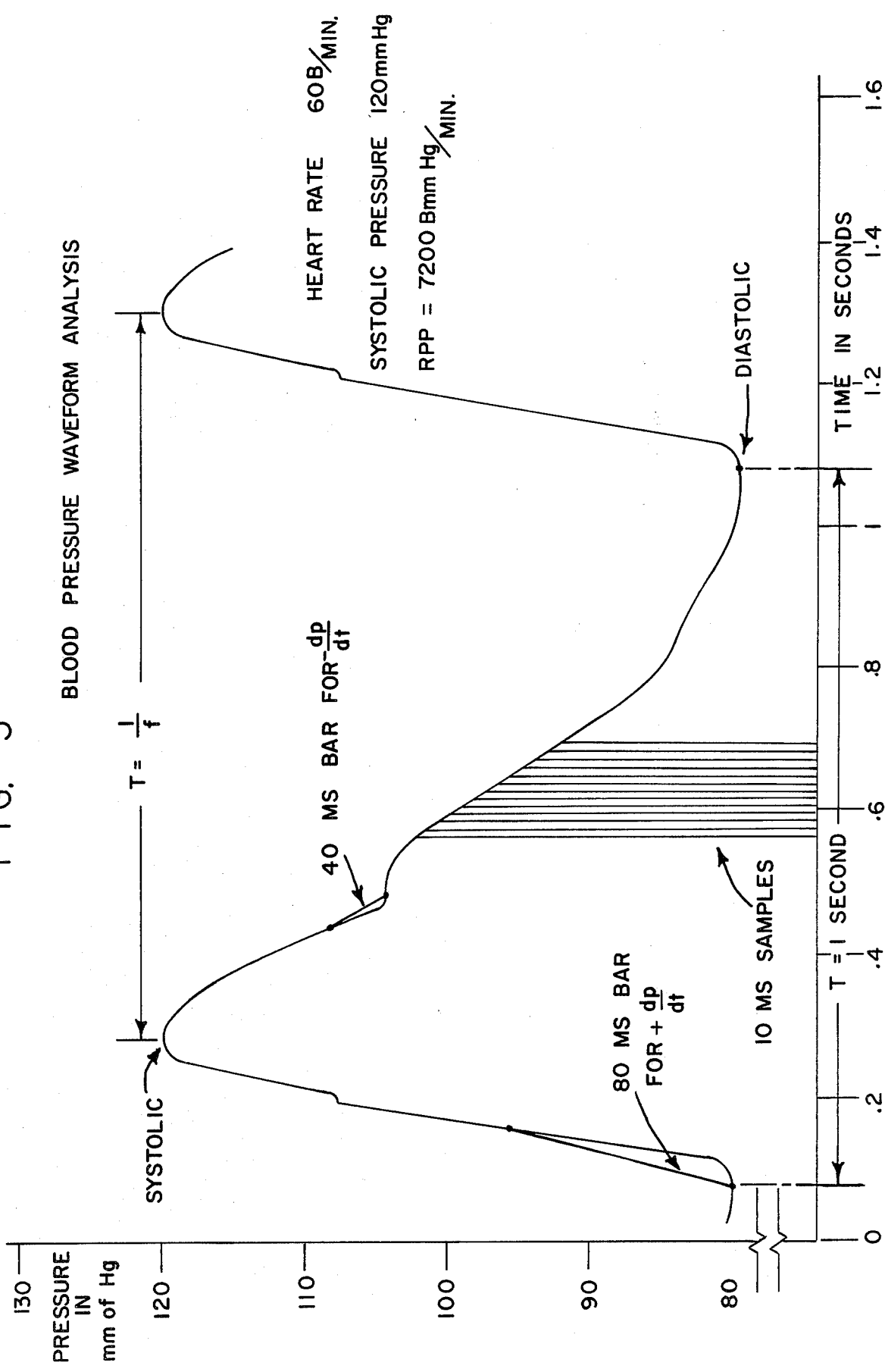
FIG. 5 is a graph diagram showing a typical blood pressure waveform.

The software flowchart is shown in FIG. 4. Once the computer is activated the RAM units 34 are initialized to contain the proper flags. An RST7.5 interrupt is then enabled in the CPU 31 to respond when the 10 millisecond signals are received from the timer 36. Upon encountering an interrupt the CPU 31 informs the A/D converter 38 to digitize the incoming blood pressure signal into an 8-bit code and the keyboard 20 is scanned for a depressed key. When a key is pressed, the computer enters into a routine which allows the user to check and/or reset the high and low rate-pressure product alarm settings, the beat averaging, and the input level. Initially, the high rate-pressure product alarm setting is set to 65536, the low alarm setting to zero, and the beat averaging alarm setting to one. When keyboard operation is not desired, the computer enters into the analysis portion of the blood pressure waveform.

The analysis on the waveform can be seen in FIG. 4. Two "bars" are formed to slide along the waveform. An 80 millisecond bar, made up of eight 10.0 millisecond samples, is used for the systolic peak and a 40 millisecond bar, made up of four 10.0 millisecond samples is used for the diastolic occurrence. The computer uses the 80 millisecond bar to trigger the point of an occurrence of the oncoming systolic peak. In an examination of approximately 100 human blood pressure waveforms it was found that a systolic peak could be detected if the slope of the 80 millisecond bar was equal to or greater than 16 mmHg/80 ms. From that point on, no matter what the value of the bar (after it has first triggered the search for the systolic) the computer continues to sample for the maximum pressure and for the time of its occurrence. This continues until the 40 millisecond bar reaches a value equal to or less that −5 mmHg/40 ms. This slope value, like the 80 millisecond bar, was found by the analysis of human blood pressure waveforms. Using both of these bar lengths and slopes, noise (catheter whip, etc.) or abnormalities in the waveform would not trigger the computer on false peaks.

Once the diastolic bar value of 5 mmHg/40 ms is reached, the computer stops its sampling of the waveform and computes (from the samples previously received) the heart rate, systolic pressure, and diastolic pressure. The timer 36 is the clock for the heart rate and sampling portion of the program. Once the second systolic peak is established the computer calculates the elapsed value between systolic pressures of the 1000 Hz timer and divide that into 60,000 to get the rate in beats/minute. When all these values are computed, the beat averaging value is checked. If the user sets the beat averaging greater than one, the computer returns and begins sampling the waveform once again until the predetermined number of cycles has been reached. After this occurs, the averaged heart rate and systolic pressure is multiplied together and its product, the RPP, compared to the present alarm values. If the value of the RPP exceeds the limits set two times in a row then the alarm is triggered (audio beeper 58 and a LED 56). This allows for an ectopic beat which occurs in some patients. The computer then updates the display with the proper values of the heart rate, systolic and diastolic blood pressure, and the RPP. The computer returns, reinitializes the RAM, and starts sampling again for the next display.

Noise from catheter whip and abnormalities in the waveform do not cause the computer to register any false peaks. This can be attributed to the 80 millisecond bar which must be at least 16 mmHg/80 ms or else the computer would not search for a systolic peak. Any noise that occurs is usually on the order of five to ten milliseconds long with a small magnitude. The 80 millisecond bar was selected to prevent triggering on these noise pulses.

GENERAL OPERATION

The initial set-up of the monitor using the HP 8805B amplifier 15 is very simple. The operator first initializes amplifier 15 so that it is functioning correctly. Then amplifier 15 is then plugged into the computer. The computer switch 27 is then turned on and the front panel input switch 26 put on the "HP" setting. In order to initialize the computer, the operator depresses key "A" which halts any computations and enters the computer into the keyboard mode. When the key is depressed, the "KYBD" light goes on. The next key to be depressed in this initialization period is the "#" key which is used to bring the computer into the input level checking mode. This too causes the "LEV-CHK" light to be on reminding the operator of the mode the computer is in. Next, the operator sets the carrier amplifier to output a signal corresponding to zero mmHg. When this is done the operator adjusts the "zero" control on the back of the computer until a "1" is seen on the systolic display of the front panel. This is done because a "1" is the lowest number that could be displayed without blanking the screen. If desired, the level shifting may be turned slightly more until the screen actually blanks i.e. a zero has been reached. The carrier amplifier is then set to output 250 mmHg. Now, the "gain" control on the back of the computer is adjusted so that the systolic display reads "250." The "#" key is pressed first and then the "A" key is pressed. This puts the computer back in normal operation. If the carrier amplifier is once again set to output the blood pressure waveform, the computer will accurately monitor and display the heart rate, systolic pressure, diastolic pressure, and rate-pressure product of the patient involved.

The keyboard on the front panel is operated in the same fashion no matter which input is being utilized for the blood pressure waveform signal. This keyboard is used to change the initial high and low rate-pressure product alarm settings, monitor the input signal, and set the beat averaging. Initially there should only be one LED lite up on the bottom of the front panel over the "POWER" label. The keyboard is designed not to function unless key "A" is first depressed. The depression of this key will cause the computer to stop what it is doing and enter into the keyboard mode. The "KYBD" light should be on to show the operator that he/she may continue.

Keys B and C control the high and the low rate-pressure product alarm settings. When key B is depressed, the "HI-SET" light on the front panel is turned on and the old high rate-pressure product alarm setting is displayed on the "RATE-PRESSURE PRODUCT" space on the front screen. If the operator wants to leave this alarm setting unchanged, he/she presses the clear key, labeled "x." The old alarm setting will be put back into the memory and an exit out of the HI-SET mode will occur. If on the other hand the alarm setting is to be changed, the operator types in a number less than or equal to 65,535. Then, upon the depression of key "B" the contents displayed on the screen are placed in memory. Also, if some new numbers were being entered and the operator changes his/her mind and decides to save the old number, all that need be done is to depress the "x" key and the old alarm setting will remain unchanged. This same process is used to set the low rate-pressure product alarm setting. If these boundries set up by the alarms are crossed two consecutive times, the LED alarm light 56 will go on. Depending on whether the audio alarm switch 28 located on the front panel is on, buzzer 58 will also be actuated. The reason for the presence of allowing one error to occur on the alarm boundries is that sometimes in sick patients it is quite normal for their heart to skip a beat. They call this an ectopic beat. To minimize the occurrence of false alarms the computer is designed to activate the alarm signals only upon seeing two errors, not just one prolonged heart beat such as that caused by an ectopic beat.

Another feature incorporated into the computer is the ability to do beat averaging along with beat to beat real time computations. By depressing key "D" while in the keyboard mode, the averaging can be set from one to two-hundred fifty-five beats. All that is required is to press the numbers desired, depress the "D" key, and exit out of the keyboard with key "A." The operation of the clear key, "x," applies here as to the alarm settings described above. By the careful setting of the averaging, a stable yet still precise reading of all the parameters will occur. The upper limit to the averaging is set to 255. If a number greater than this is entered, the averaging will be automatically set to the difference between the number keyed in and 255 until the resultant is less than 255.

There is also a key on the keyboard which is identified by the symbol "#." This key is used to set the computer to just continuously sample the input at a rate greater than 1000 Hz and display the input in BCD on the systolic pressure display on the front panel. By the depression of this key the precise condition of the input signal is shown.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. Vital signs monitor comprising:
 (a) a sensor for sensing the heart beat and blood pressure of a patient and producing electrical pulses in a waveform indicative of the heart rate, systolic blood pressure, and diastolic blood pressure,
 (b) a computer for receiving the electrical waveform pulses from the sensor, converting the waveform pulses into digital signals and calculating a rate-pressure product which is the product of the heart rate and the systolic blood pressure, said computer comprising:
  (1) control means for counting the heart beats of the patient, averaging the heart rate, blood pressure and rate-pressure product for a plurality of heart beats and causing said averaged rate-pressure product valve to be displayed on the display screen,
  (2) a heart beat memory connected to the control means for determining the number of heart beats that constitute the rate-pressure product averaging value to be displayed on the screen,
  (3) keyboard control switches for programming the heart beat memory to set the number of heart beats to be averaged, and
  (4) a digital display screen connected to the computer for visually displaying the heart rate, blood pressure and rate-pressure product in digital form.

2. Vital signs monitor as recited in claim 1, wherein the computer comprises:
(a) an alarm,
(b) an alarm memory connected to the alarm, and
(c) keyboard control switches for programming the alarm memory for a high-rate pressure product value and a low rate-pressure product value so that the alarm is activated when the display screen shows said high value or said low value, and wherein the digital display screen includes light emitting diode numerical units.

3. Vital signs monitor as recited in claim 2, wherein said alarm comprises:
(a) a light on the display screen, and
(b) an audio element.

4. Vital signs monitor as recited in claim 3, wherein the computer includes an alarm switch for selectively connecting and disconnecting the audio element from the alarm.

5. Vital signs monitor as recited in claim 1, wherein the sensor is a catheter transducer unit for application to a principal artery of the patient.

* * * * *